(12) United States Patent
Hui et al.

(10) Patent No.: US 9,921,198 B2
(45) Date of Patent: Mar. 20, 2018

(54) METHOD TO DETERMINE THE CROCETIN AND ITS DERIVATIVE AMOUNTS AND THE DERIVATIVE COMPOSITION FROM GARDENIA YELLOW

(71) Applicant: Henan Zhongda Biological Engineering Co., Ltd., Zhengzhou, Henan Province (CN)

(72) Inventors: Bodi Hui, Zhengzhou (CN); Ping Gong, Zhengzhou (CN); Yanjun Wen, Zhengzhou (CN); Linzheng Li, Zhengzhou (CN); Tianyi Pan, Zhengzhou (CN); Honglong Li, Zhengzhou (CN); Wenjin Zhang, Zhengzhou (CN); Ziheng Jin, Zhengzhou (CN)

(73) Assignee: HENAN ZHONGDA BIOLOGICAL ENGINEERING CO. LTD., Zhengzhou (CN)

( * ) Notice: Subject to any disclaimer, the term of this patent is extended or adjusted under 35 U.S.C. 154(b) by 0 days.

(21) Appl. No.: 15/298,962

(22) Filed: Oct. 20, 2016

(65) Prior Publication Data

US 2017/0248561 A1   Aug. 31, 2017

(30) Foreign Application Priority Data

Feb. 29, 2016   (CN) .......................... 2016 1 0124837

(51) Int. Cl.
G01N 30/02 (2006.01)
G01N 30/86 (2006.01)
G01N 30/72 (2006.01)

(52) U.S. Cl.
CPC ..... *G01N 30/8679* (2013.01); *G01N 30/7233* (2013.01); *G01N 2030/027* (2013.01)

(58) Field of Classification Search
CPC ........... G01N 30/8679; G01N 30/7233; G01N 2030/02
See application file for complete search history.

(56) References Cited

FOREIGN PATENT DOCUMENTS

CN   101863754 A  * 10/2010
CN   104402702 A  *  3/2015

* cited by examiner

*Primary Examiner* — Mischita Henson
(74) *Attorney, Agent, or Firm* — Troutman Sanders LLP

(57) ABSTRACT

The invention relates to a method for the determination of crocetin and its derivative amounts and the derivative composition from *gardenia* yellow. The method mainly comprises of following steps: the absorbance measurement of a *gardenia* yellow aqueous solution at known concentration by UV-VIS, the absorption coefficient measurement of total crocetin derivative, the total crocetin derivative amount calculation according to Lambert-Beer law, the relative amount calculation of each crocetin derivative from its absorption coefficient and peak area on HPLC, the amount calculation of each crocetin derivative from the total amount of crocetin derivative and the relative amount of each crocetin derivative, and finally total crocetin amount calculation. In practice, the absorption coefficient of each crocetin derivative is calculated from that of its root structure, crocetin, based on the negative correlation-ship of absorbance with molecular mass of the molecule while the molecular mass of each crocetin derivative is substituted by the m/z value of its parent ion.

1 Claim, 2 Drawing Sheets

METHOD TO DETERMINE THE CROCETIN AND ITS DERIVATIVE AMOUNTS AND THE DERIVATIVE COMPOSITION FROM GARDENIA YELLOW

This application claims the benefit of Chinese Patent Application Ser. No. 201610124837.6, filed Feb. 29, 2016, entitled "A METHOD TO DETERMINE THE CROCETIN AND ITS DERIVATIVE AMOUNTS AND THE DERIVATIVE COMPOSITION FROM *GARDENIA* YELLOW," the entire contents and substance of which are hereby incorporated by reference as if fully set forth below.

TECHNICAL FIELD

The various embodiments of the disclosure relate generally to determine the crocetin and its derivative amounts and the derivative composition from *gardenia* yellow. processes,

BACKGROUND

*Gardenia* yellow is a product that is usually used in foods as a colorant under the category of food additive in Asian countries, especially in eastern Asian countries such as China, Japan and South Korea.

The product is the fruit extract of *Gardenia jasminoides* Ellis by alcohol and usually comprises more than 20 species of crocetin derivatives, mainly esters, but not a single compound. A chemical or an IUPAC name of the product is not available. Only recommended common name is applied. As the major crocetin ester, crocin is defined as a di-ester typically formed from gentiobiose and crocetin, including crocin-I (Crocetin-di-beta-D-gentiobiosyl ester), crocin-II (Crocetin-beta-D-gentiobiosyl-beta-D-glucosyl ester), crocin-III (Crocetin-mono-beta-D-gentiobiosyl ester), crocin-IV (beta-D-monoglucoside ester of monomethyl alpha-crocetin) and so on.

The molecular formulae of crocetin and crocin are $C_{20}H_{24}O_4$ and $C_{44}H_{64}O_{24}$, respectively. The formula masses of crocetin and crocin are 328.40 and 976.96, respectively. C.A.S numbers of crocetin and crocin are 27876-94-4 and 42553-65-1, respectively. The molecular structures of crocetin, crocetin ester and crocin are shown in Structures I, II, and III. Double bonds presented in the central polyene chain of crocetin and its derivative can result in the E- or Z-isomerization of the molecules. In Nature, the majority of crocetin and its derivative exist in all-E-configuration while the Z-isomer also can be found in minor amount.

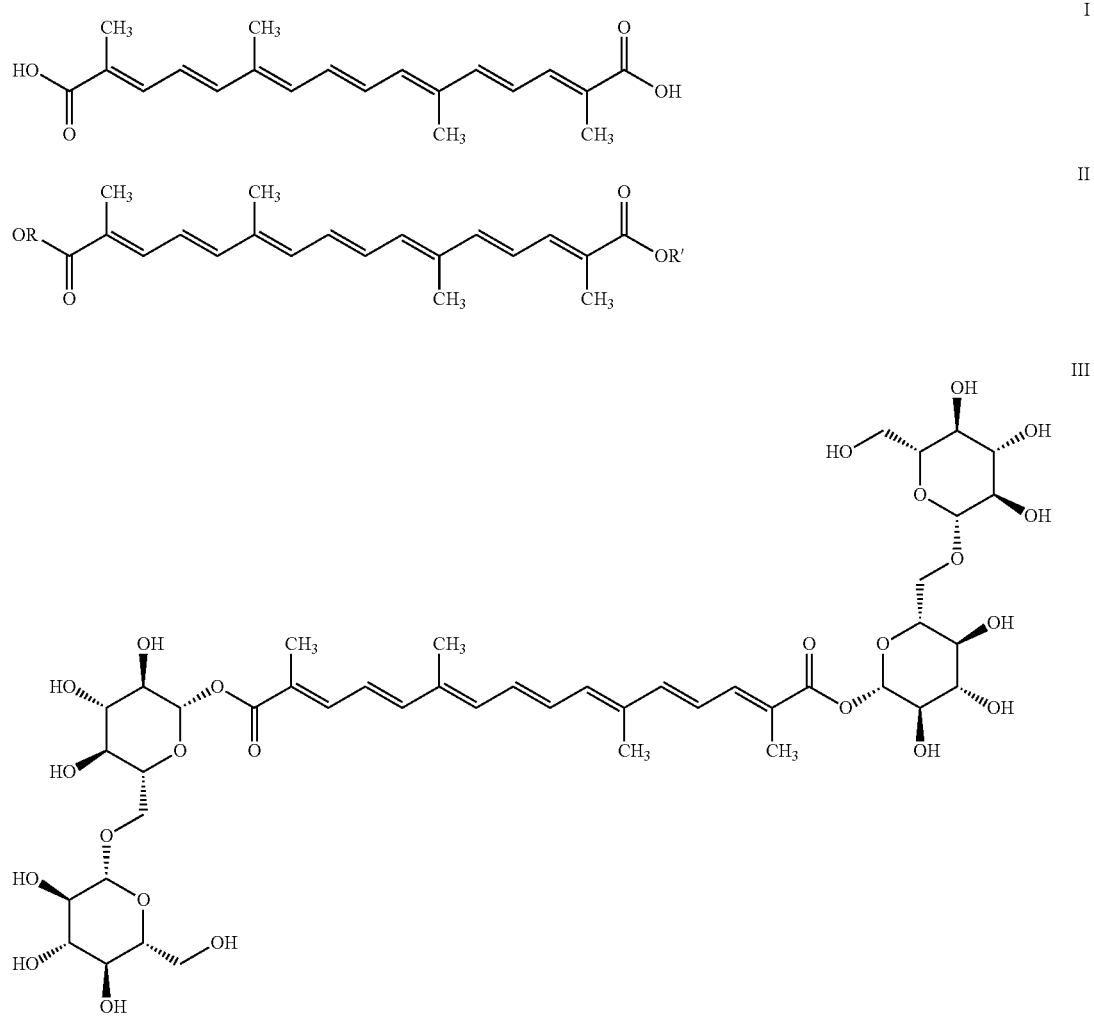

Physical and Chemical Features

*Gardenia* yellow is a free-flowing powder that exhibits color from yellow to orange, smells a slight odor of fruit from *Gardenia jasminoides* E. and tastes slight bitter. The product is stable under neutral pH condition.

*Gardenia* yellow is freely soluble in water, slightly soluble in ethanol and insoluble in hexane. After the addition of 2 mL sulfuric acid into 0.5 g sample, sample color converted from deep blue to purple and finally to brown slowly. The pH value of 1% water solution is usually between 5.5 and 7.5. If heating temperature 101-105° applied for not less than 2 hours, it is dried to constant weight.

Raw materials to produce *gardenia* yellow is the fruit of *Gardenia jasminoides* E. Originated in Asia, very possible in southern China, *Gardenia jasminoides* is a tropical plant and most commonly found in southern China, Vietnam and India. Apart from wild type, the plant was cultured by Chinese very possibly since Song Dynasty (960-1279 AD), because some traditional Chinese paintings had depicted this plant since then (Keswick, M. 2003; Valder, P. 1999). This plant was introduced to Britain in 1750's. The plant was botanically described at the first time by English botanist John Ellis in 1761 (Foster, S, and Yue, C. 1992).

The plant is a shrub with dark green shiny leaves. The white flowers bloom from spring to summer and are followed by small oval fruit. Due to its shiny green leaves and fragrant flowers, it was widely cultured in gardens. As a tropical plant, it prefers warm and humid climate conditions. However, it likes indirect sunlight and shade rather than direct sunlight. It is an acidophile plant and likes acidic soils. For its better growing, farmers even had lower soil pH by vinegar (Gilman, E. F. 1999). Many cultivars have been developed.

China is the major culture base of *Gardenia jasminoides* E. In 2015, more than 10,000 tons of the fruits were collected from P. R. China. The collected fruits were processed following two major ways. One was for medical use and the other was for food colorant. Some varieties or cultivars with smaller fruit and higher geniposide amount are good for medical use. The other varieties or cultivars with larger fruit and lower geniposide content are better for pigment extraction. The annual outputs of medical-use and food colorant-consuming fruits were 4,000-5,000 and 6,000-7,000 tons, respectively, in 2015. The average amount of crocin from the food colorant-consuming fruits is 0.45% (W/W). The 30-32 tons of pure crocin were therefore able to be produced every year from P. R. China.

China is also the major producer of *gardenia* yellow. For more than 30 years, Chinese have prepared *gardenia* yellow from the fruit of *Gardenia jasminoides* E. After purification, the extract was used in foodstuffs as colorant. China, at the moment, is the largest producer of *gardenia* yellow in the world.

Usually, dried the fruit of *Gardenia jasminoides* is ground to form fine pieces. Ground pieces are extracted with 95% (V/V) alcohol (food grade). The extract is further concentrated by macro-porous resins. A spray drying is then applied to form final product, colorant powders. The final product usually has the crocin (crocetin plus 2 gentibiosides) amount of 45-55% (W/W) and geniposide amount less than 0.5% (W/W). No harmful chemicals applied in whole process. Most toxic chemicals were involved in manufacturing. Most manufacturers were able to perform GMP, ISO and HACCP schemes simultaneously to guarantee the quality and safety of the final products.

The fruit extract of *Gardenia jasminoides* E. has been used as a yellow pigment to color clothes and foodstuffs for a long history. Apart from pigment resource, *Gardenia jasminoides* E. is also recognized as a traditional herb by Chinese. The fruit of the plant used be one of the most popular traditional Chinese medicines. In Chinese Pharmacopoeia (Version 2015), the fruit of *Gardenia jasminoides* E. was recorded as 'Fructus *Gardeniae* from *Gardenia jasminoides* E. to have "drain fire" function and treat certain febrile conditions. Its recommended daily intake is 6-9 grams. The functional component of raw materials is geniposide. The average amount of geniposide is 3-5% (W/W). Information from Chinese Pharmacopoeia (Version 2015) indicates that a maximum daily intake of 450 mg geniposide is allowed.

BRIEF SUMMARY

The various embodiments of the disclosure relate generally to processes, methods, and systems for processing and characterizing solution of *gardenia* yellow composed of many different compounds.

An embodiment of the disclosure can include the following steps: producing an aqueous solution of *gardenia* yellow, separating the solution into a plurality of fractions using high performance liquid chromatography, measuring absorbance and molecular weight of each of the fractions using a photo-diode array coupled to an atmospheric pressure chemical ionization MS-MS.

Embodiments of the disclosure can additionally include measuring absorbance of the aqueous solution before separating the solution into the plurality of fractions. The embodiments may also be characterized by separating the solution of *gardenia* yellow using a column for reversed-phase separation.

In an embodiment of the disclosure, the aqueous solution of *gardenia* yellow can be composed of many crocetin derivatives. These crocetin derivatives can be separated as described in the Embodiments provided so that each of the separate fractions comprises a crocetin derivative characterized by a measured molecular weight and a peak area.

Additionally embodiments of the disclosure provide a method to determine the absorption coefficient of total crocetin derivative. The absorption coefficient of total crocetin derivative can be calculated as a weighted sum of a corrected absorbance coefficient of crocetin for each crocetin derivative. In certain embodiments, the corrected absorbance coefficient of crocetin for each crocetin derivative may be determined as the ratio of the molecular weight of crocetin to the molecular weight of the crocetin derivative, multiplied by the absorbance of a 1% (W/V) crocetin solution in a cell of 1 cm path-length monitored at 440 nm. In other embodiments the absorption coefficient of total crocetin derivative can be calculated by a sum of each crocetin derivative peak area multiplied by the corrected absorbance coefficient of each crocetin derivative, divided by the sum of all crocetin derivative peak areas.

An embodiment of the disclosure can include a method for analysis of a mixture of crocetin compounds, the mixture of crocetin compounds being derived from an extract of fruit of a *Gardenia jasminoides* Ellis. This method includes the steps of preparing an aqueous solution of the mixture of crocetin compounds, separating the mixture of crocetin compounds into a plurality of individual fractions comprising a crocetin species using reversed phase high-performance liquid chromatography, characterizing each of the crocetin species by determining an absorption peak area at 440 nm ($P_i$) and a molecular mass ($M_i$), calculating a crocetin species absorption coefficient ($A_i$) by multiplying a standard absorption coefficient for crocetin ($A_{crocetin}$) by a ratio of a molecular mass of crocetin to the crocetin species molecular mass ($M_{crocetin}/M_i$), determining a total crocetin absorption coefficient ($A_{total}$) by multiplying the crocetin species absorption coefficient by the crocetin species absorption peak area divided by a sum of all the crocetin species absorption peak areas and summing this value over all of the crocetin species.

$$A_{total} = \sum_i \frac{A_{crocetin}\left(\frac{M_{crocetin}}{M_i}\right)P_i}{\Sigma P_i}$$

Embodiments of the disclosure can additionally include determining the absorbance of the mixture of crocetin compounds before separation (A). The embodiments of the disclosure may also include substituting the molecular mass of each crocetin derivative with its measured parent ion $[M-1]^-$ mass reading [m/z] from MS.

Some embodiments of the disclosure may include measuring the absorption peak area at 440 nm using a photodiode array detector. Embodiments may also include measuring molecular mass using an atmospheric pressure chemical ionization mass spectrometer.

In certain embodiments it is contemplated that the characterizing step can be performed simultaneously with the separating step. Further some embodiments can include determining the amount of total crocetin derivative in the mixture of crocetin compounds.

A further embodiment of the disclosure may include a method of determining total crocetin content from a mixture of crocetin derivatives, including the steps: preparing an aqueous solution of the mixture of crocetin derivatives, determining the absorbance of the mixture of crocetin derivatives (A), separating the mixture of crocetin derivatives into a plurality of individual fractions comprising a crocetin species using reversed phase high-performance liquid chromatography, characterizing each of the crocetin species by determining an absorption peak area at 440 nm ($P_i$) and a molecular mass ($M_i$), calculating a crocetin species absorption coefficient ($A_i$) by multiplying a standard absorption coefficient for crocetin ($A_{crocetin}$) by a ratio of a molecular mass of crocetin to the crocetin species molecular mass ($M_{crocetin}/M_i$), determining a total crocetin absorption coefficient ($A_{total}$) by multiplying the crocetin species absorption coefficient from step (iv) by the crocetin species absorption peak area from step (iii) divided by a sum of all the crocetin species absorption peak areas from step (iii) and summing this value for all of the crocetin species.

$$A^{1\%}_{1cm\,Total\,crocetin\,derivstive} = \sum_i \frac{A_{crocetin}\left(\frac{M_{crocetin}}{M_i}\right)P_i}{\Sigma P_i}$$

Additional embodiments may include calculating the total crocetin content according to the Beer-Lambert relationship, wherein the total crocetin absorption coefficient is used as a proxy for molar absorptivity.

Embodiments of the disclosure can include a method to determine derivative amounts and composition of crocetin in *Gardenia* yellow. The method includes the following steps:

(i) dissolving M grams *gardenia* yellow powder dissolved in V mL in water, which is then diluted by water to N-fold, and the absorbance (A) of diluted sample solution recorded at the wavelength of 440 nm, (ii) acquiring a chromatographic profile of *gardenia* yellow aqueous solution of the sample aqueous solution, by filtering an aliquot of *gardenia* yellow aqueous solution before dilution on 0.45µ filter, injecting onto an HPLC with C18-HPLC column, the fractions of crocetin, its derivatives and other pigments separated under conditions that can include a stationary phase using a reversed phase C18 column (250×4.6 mm, 5 µm); a mobile phase using solvent A: water-acetonitrile-acetic acid at 74.95:25:0.05 (V/V/V); solvent B: acetonitrile; and a linear gradient elution of mobile phase B from 0 to 13.1% (V/V) in 20 minutes, and isocratic elution from 20 to 35 minutes. The separation can be conducted at a flow rate: 0.8 mL/min, an Injection volume of 20 µL and a column temperature at substantially room temperature;

In any of the above embodiments the absorbance monitoring wavelength can be 440 nm, and the electronic absorption spectrum of each fraction is acquired from 250 to 700 nm for fraction identification if a PDA equipped, and the peak are of each fraction can be obtained by integration of the chromatogram.

Any of the above embodiments may also include identifying, on a C18-HPLC-PDA-APCI-MS-MS, each fraction containing crocetin structure as crocetin derivative, usually as crocetin ester, on the HPLC-MS under the chromatographic conditions as outlined above and MS conditions comprising: Spray voltage: −4 Kv; Sheath gas: 30 arb; Auxiliary gas: 10 arb; Purge gas: 0 arb; Capillary temperature: 350° C.; Negative ion detection mode: Data dependency scan; CID collision energy: 35%; Fragment mass scanning range: 150-2000 (m/z).

Any of the above embodiments may also include identifying the parent ion and m/z value of each crocetin derivative on MS and can further include calculating the relative peak area (%) of each crocetin derivative according to formula (1).

$$\text{Relative peak area}_i = \frac{\text{Peak area}_i}{\Sigma_{i=1}^{n} \text{Peak area}_i} \quad (1)$$

Where

Relative peak area$_i$=Relative peak area of crocetin derivative i in total crocetin derivative Peak area$_i$=Peak area of crocetin derivative i i=Fraction number of crocetin derivative n=Total number of crocetin derivative Any of the above embodiments may also include calculating the absorption coefficient of each crocetin derivative from published absorption coefficient, $A_{1cm}^{1\%}$=3820 (in EtOH), of crocetin as root structure, in accordance with the negative dependence of crocetin derivative UV-VIS absorbance on its side-chain quantity and mass indicated by molecular mass, as shown in formula (2), where the molecular mass of each crocetin derivative is substituted by its measured parent ion $[M-1]^-$ mass reading [m/z] from MS.

$$A_{1cm_i}^{1\%} = A_{1cm_{crocetin}}^{1\%} \times \frac{\text{Molecular mass}_{crocetin}}{\text{Molecular mass}_i} \quad (2)$$

Where
$A_{1cm_i}^{1\%}$=Absorbance coefficient of crocetin derivative i, defined as the theoretical absorbance of a 1% (W/V) crocetin derivative i solution in a cell of 1 cm path-length at monitored 440 nm.

$A_{1cm_{Crocetin}}^{1\%}$=Absorbance coefficient of crocetin, defined as the theoretical absorbance of a 1% (W/V) crocetin solution in a cell of 1 cm path-length monitored at 440 nm. Published value of 3820 (in methanol) is applied hereon.

Molecular mass$_{crocetin}$=Molecular mass of crocetin. Published value of 328 is applied hereon.

Molecular mass$_i$=Molecular mass of crocetin derivative i. Molecular mass of each crocetin derivative is hereon substituted by its parent ion mass [m/z] from MS.

i=Fraction number of crocetin derivative

Any of the above embodiments may also include calculating the absorption coefficient of total crocetin derivative by weighted sum from the relative peak area and absorption coefficients of each crocetin derivative as the results of formulae (1) and (2), respectively, according to formula (3).

$$A_{1cm_{Total\ crocetin\ derivative}}^{1\%} = \Sigma_{i=1}^n \text{Relative peak area}_i \times A_{1cm_i}^{1\%} \quad (3)$$

Where
Relative peak area$_i$=Relative peak area of crocetin derivative i $A_{1cm_{Total\ crocetin\ derivative}}^{1\%}$=Absorption coefficient of total crocetin derivative, defined as the theoretical absorbance of a 1% (W/V) total crocetin derivative solution in a cell of 1 cm path-length monitored at 440 nm.

$A_{1cm_i}^{1\%}$=Absorbance coefficient of crocetin derivative i, defined as the theoretical absorbance of a 1% (W/V) crocetin derivative i solution in a cell of 1 cm path-length monitored at 440 nm.

i=Fraction number of crocetin derivative
n=Total number of crocetin derivative

Any of the above embodiments may also include calculating the relative content of total crocetin derivative in total pigment from the peak area of each fraction monitored at 440 nm according to formula (4).

$$\text{Relative content}_{Total\ crocetin\ derivative} = \frac{\Sigma_{i=1}^n \text{Peak area}_i}{\Sigma_{j=1}^m \text{Peak area}_j} \quad (4)$$

$$C_{Total\ ester}[\%] = \frac{\Sigma_{i=1}^m Fi}{\Sigma_{j=1}^n Fj}$$

Where
Relative content$_{Total\ crocetin\ derivative}$=Relative content of total crocetin derivative in total pigment
Peak area$_i$=Peak area of crocetin derivative i
Peak area$_j$=Peak area of fraction j
i=Fraction number of crocetin derivative
n=Total number of crocetin derivative
j=Fraction number
m=Total fraction number Any of the above embodiments may also include calculating the amount of total crocetin derivative in gardenia yellow sample according to Lamber-Beer law from the absorbance of gardenia yellow aqueous solution, the relative content of total crocetin derivative in total pigment and the absorption coefficient of total crocetin derivative, as shown by formula (5).

$$\text{Amount}_{Total\ crocetin\ derivative}[g] = \frac{A \times \text{Relative content}_{Total\ crocetin\ derivative} \times V \times N}{A_{1cm_{Total\ crocetin\ derivative}}^{1\%} \times 100} \quad (5)$$

Where
Amount$_{Total\ crocetin\ derivative}$[g]=Amount of total crocetin derivative in gardenia yellow sample
A=Absorbance of sample solution
V=Solvent volume for sample originally dissolving
N=Dilution fold of sample solution
Relative content$_{Total\ crocetin\ derivative}$=Relative content of total crocetin derivative in total pigment
$A_{1cm_{Total\ crocetin\ derivative}}^{1\%}$=Absorption coefficient of total crocetin derivative, defined as the theoretical absorbance of a 1% (W/V) total crocetin derivative solution in a cell of 1 cm path-length monitored at 440 nm.

Any of the above embodiments may also include calculating the content of total crocetin derivative in gardenia yellow sample from the amount of total crocetin derivative and sample weight (M) according to formula (6).

$$\text{Content}_{Total\ crocetin\ derivative}[\%] = \frac{\text{Amount}_{Total\ crocetin\ derivative}}{M} \times 100\% \quad (6)$$

Where
Content$_{Total\ crocetin\ derivative}$[%]=Content of total crocetin derivative in gardenia yellow sample
Amount$_{Total\ crocetin\ derivative}$[g]=Amount of total crocetin derivative in gardenia yellow sample
M=Mass of gardenia yellow sample Any of the above embodiments may also include calculating according to Lamber-Beer law, the relative content of each crocetin derivative in total crocetin derivative from the peak area (Section A.2) and absorption coefficients of each crocetin derivative (Section A.6), as shown by formula (7).

$$\text{Relative content}_i[\%] = \frac{\frac{\text{Peak area}_i}{A_{1cm_i}^{1\%}}}{\Sigma_{i=1}^n \frac{\text{Peak area}_i}{A_{1cm_i}^{1\%}}} \times 100\% \quad (7)$$

Where
Relative content$_i$=Relative content of each crocetin derivative in total crocetin derivative
Peak area$_i$=Peak area of crocetin derivative i
i=Fraction number of crocetin derivative
n=Total number of crocetin derivative Any of the above embodiments may also include calculating the amount of each crocetin derivative from gardenia yellow sample from the relative content of each crocetin derivative and the amount of total crocetin derivative according to formula (8).

$$\text{Amount}_i[g] = \text{Relative content}_i \times \text{Amount}_{Total\ crocetin\ derivative} \quad (8)$$

Where
Amount$_i$=Amount of each crocetin derivative from gardenia yellow sample
Relative content$_i$=Relative content of each crocetin derivative in total crocetin derivative
Amount$_{Total\ crocetin\ derivative}$=Amount of total crocetin derivative in gardenia yellow sample
i=Fraction number of crocetin derivative.

DETAILED DESCRIPTION

Figure 1:
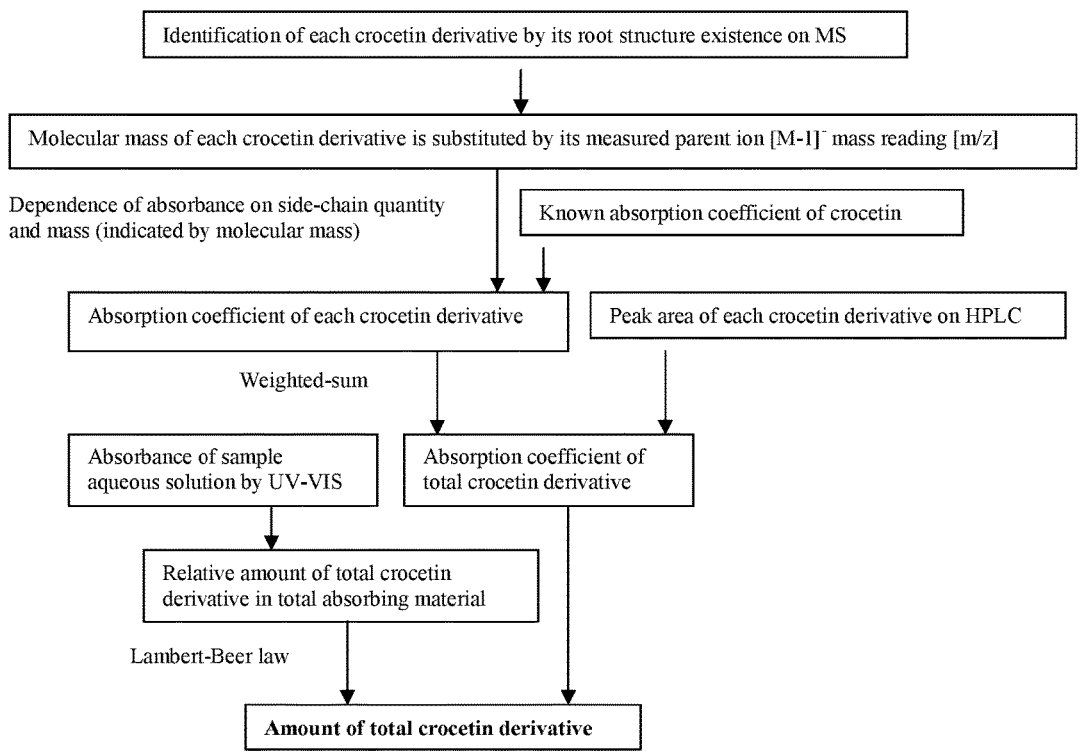
FIG. 1 illustrates a flow chart for determining the total amount of crocetin derivative amount, in accordance with an exemplary embodiment of the disclosure.
Figure 2:
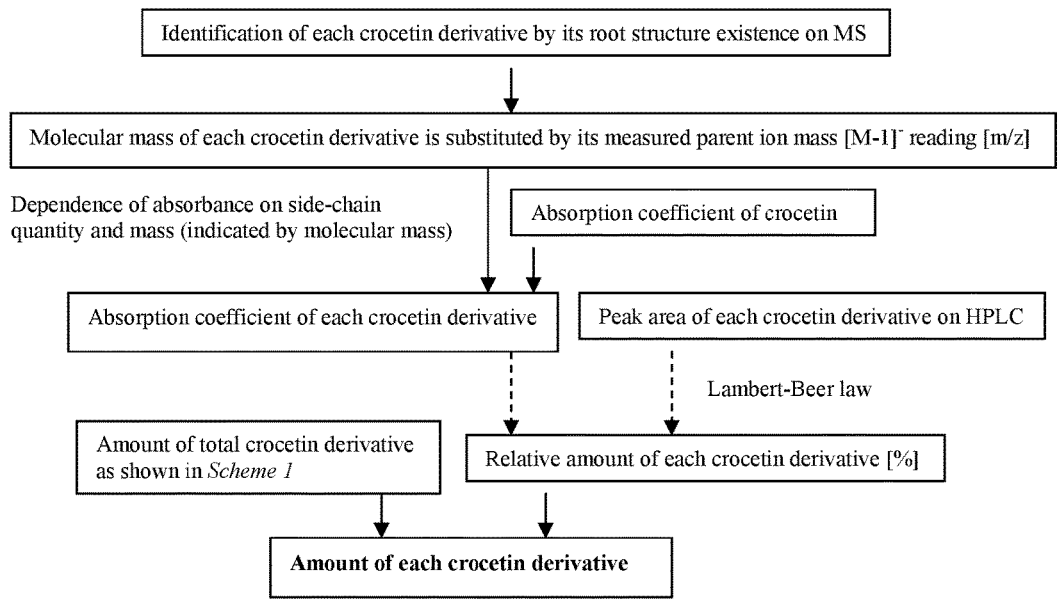
FIG. 2 illustrates a flow chart for determining each crocetin derivative amount in accordance with an exemplary embodiment of the disclosure.
Figure 3:
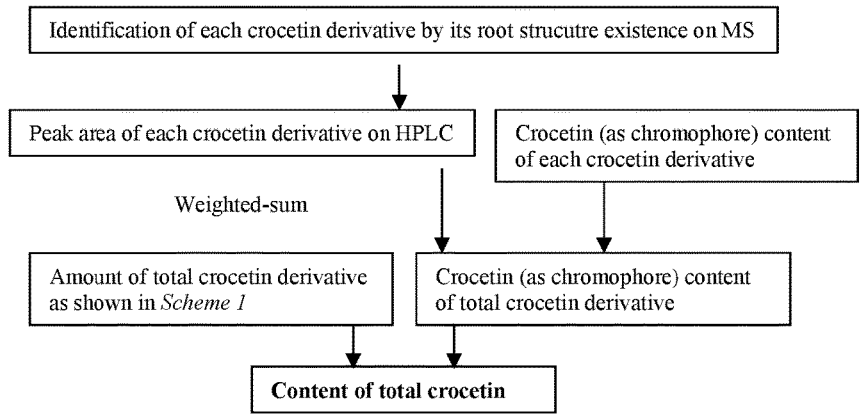
FIG. 3 illustrates a flow chart for determining the amount of crocetin in accordance with an exemplary embodiment of the disclosure.

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

For the *gardenia* yellow product quality control scheme, UV-VIS spectroscopic method, given in China National Food Safety Standards, Food additive, *Gardenia* yellow, for the specific absorption coefficient assessment of total crocetin derivative and other pigments was applied. In some cases, C18-HPLC method for crocin amount determination may be employed.

(1) UV-VIS Spectroscopic Method for the Specific Absorption Coefficient

The accurately weighed amount of *gardenia* yellow is dissolved in an aliquot of water and methanol mixture (1:1, V/V) to prepare a sample solution at a fixed concentration. The absorbance of final diluted sample solution is measured at 440±5 nm in a 1 cm cuvette on UV-VIS spectrophotometer, with water as control. The specific absorption coefficient of the sample is calculated as follow:

$$E_{1cm}^{1\%}(440 \pm 5)\text{nm} = \frac{A}{C} \times \frac{1}{100}$$

Where $E_{1cm}^{1\%}(440\pm5$ nm): The specific absorption coefficient, is defined as the absorbance of the product solution of 1% concentration, i. e. 1 g in 100 mL, in a 1 cm path-length cuvette.

A: Actual absorbance of product solution

C: Concentration [g/mL] of product solution

The final result is calculated from the arithmetic mean of parallel measurements. The absolute difference of two independent observations is not more than the 5% of their arithmetic mean under the same conditions.

It is an object of this method to provide the $E_{1cm}^{1\%}(440\pm5$ nm) of the product but not total and individual component amounts.

(2) Crocin Amount Assay by HPLC

The accurately weighed amount of *gardenia* yellow is dissolved in an aliquot of water and methanol mixture (1:1, V/V) to prepare a sample solution at a fixed concentration. The external reference sample (commercialized Crocin I) is dissolved in the same solvent to make its mother and work solutions. The sample solution is introduced into C18-HPLC for fraction separation and quantification by external reference under following conditions: Stationary phase: C18 column (4.6×150 mm, 5 μm); Column temperature: 40° C.; Mobile phase A: 4 L H2O (with 0.04% TFA); Mobile phase B: Acetonitrile (with 0.0.2% TFA); Linear gradient: Mobile phase B increased from 0 to 60% in 10 minutes then to 100% in 5 minutes followed by an isocratic elution for 5 minutes; Flow rate: 1 mL/min; Monitoring wavelength: 440 nm; Sample injection volume: 5 □L.

A linear equation ($R^2$=0.9994) was obtained by correspondence of peak areas with concentrations of external reference sample. Sample with crocin concentration from 7.44 μg/mL to 119 μg/mL conforms to the linear relation. The crocin amount of *gardenia* yellow sample is then calculated from the peak area of crocin fraction and the linear equation.

While the existing analytical method to determine the absorption coefficient of *gardenia* yellow is applied to the quality control scheme of the product, it would be appreciated that the present invention provides a method to determine the crocetin content and the total amount and composition of its derivative from *gardenia* yellow. Under such circumstance, the amount of functional factors and coloring substances are determined. This effort is going to form a base to demonstrate the dose-effect relationship between the amount of functional factors and their biological functions.

It should be appreciated that the present method may be applied although the structure elucidation work of some crocetin derivatives has not finished yet from *gardenia* yellow.

The present method is easy to be performed and with a satisfied reproducibility.

To facilitate the understanding of the invention, a number of terms are herewith defined. Terms defined herein have meanings as commonly understood by a professional individual with ordinary skill in the fields that is relevant to the invention. Terms such as "a", "an" and "the" are not intended to refer to only a singular entity, but to multiple entities which a specific example may be applied. The terminology herein is used to describe specific embodiments of the invention, but their usage does not delimit the invention, except as outlined in the claims.

To achieve the objectives as indicated above, the present invention employs the following technical approaches:

A. Determination of Total Crocetin Derivative Amount

1. To determine the absorbance of *gardenia* yellow aqueous solution at known concentration, M grams *gardenia* yellow powder is accurately weighed. The sample powders are dissolved and make volume to V mL in water. The solution is then diluted by water to N-fold. The absorbance (A) of diluted sample solution is recorded at the wavelength of 440 nm.

2. To acquire the HPLC profile of sample aqueous solution, an aliquot of *gardenia* yellow aqueous solution before dilution is filtered by 0.45μ filter and immediately for HPLC injection. With C18-HPLC, the fractions of crocetin, its derivatives and other pigments are readily separated under following conditions: Stationary phase: reversed phase C18 column (250×4.6 mm, 5 μm); Mobile phase A: Water-acetonitrile-acetic acid at 74.95:25:0.05 (V/V/V), mobile phase B: Acetonitrile; Linear gradient elution: Mobile phase B from 0 to 13.1% (V/V) in 20 minutes consequently followed by an isocratic elution from 20 to 35 minutes; Flow rate: 0.8 mL/min; Injection volume: 20 μL; Column temperature: At room temperature; Monitoring wavelength: 440 nm. The electronic absorption spectrum of each fraction is acquired from 250 to 700 nm for fraction identification if a PDA equipped. The chromatographic profile of *gardenia* yellow aqueous solution is acquired on HPLC. The peak are of each fraction is integrated on the chromatogram.

3. With C18-HPLC-PDA-APCI-MS-MS, each fraction containing crocetin structure is identified as crocetin derivative, usually as crocetin ester, on the HPLC-MS under the chromatographic conditions as outlined above and MS conditions as follow: Spray voltage: −4 Kv; Sheath gas: 30 arb; Auxiliary gas: 10 arb; Purge gas: 0 arb; Capillary temperature: 350° C.; Negative ion detection mode: Data dependency scan; CID collision energy: 35%; Fragment mass scanning range: 150-2000 (m/z).

4. The parent ion is identified of each crocetin derivative on MS. The m/z value of each parent ion is recorded.

5. The relative peak area (%) of each crocetin derivative is calculated according to formula (1).

$$\text{Relative peak area}_i = \frac{\text{Peak area}_i}{\Sigma_{i=1}^n \text{Peak area}_i} \quad (1)$$

Where
Relative peak area$_i$=Relative peak area of crocetin derivative i in total crocetin derivative
Peak area$_i$=Peak area of crocetin derivative i
i=Fraction number of crocetin derivative
n=Total number of crocetin derivative 6. The absorption coefficient of each crocetin derivative is calculated from published absorption coefficient, $A_{1cm}^{1\%}$=3820 (in EtOH), of crocetin as root structure, in accordance with the negative dependence of crocetin derivative UV-VIS absorbance on its side-chain quantity and mass indicated by molecular mass, as shown in formula (2). The molecular mass of each crocetin derivative is hereon substituted by its measured parent ion [M−1]⁻ mass reading [m/z] from MS.

$$A_{1cm_i}^{1\%} = A_{1cm_{crocetin}}^{1\%} \times \frac{\text{Molecular mass}_{crocetin}}{\text{Molecular mass}_i} \quad (2)$$

Where
$A_{1cm_i}^{1\%}$=Absorbance coefficient of crocetin derivative i, defined as the theoretical absorbance of a 1% (W/V) crocetin derivative i solution in a cell of 1 cm path-length at monitored 440 nm.
$A_{1cm_{Crocetin}}^{1\%}$=Absorbance coefficient of crocetin, defined as the theoretical absorbance of a 1% (W/V) crocetin solution in a cell of 1 cm path-length monitored at 440 nm. Published value of 3820 (in methanol) is applied hereon.
Molecular mass$_{crocetin}$=Molecular mass of crocetin. Published value of 328 is applied hereon.
Molecular mass$_i$=Molecular mass of crocetin derivative i. Molecular mass of each crocetin derivative is hereon substituted by its parent ion mass [m/z] from MS.
i=Fraction number of crocetin derivative 7. The absorption coefficient of total crocetin derivative is calculated by weighted sum from the relative peak area and absorption coefficients of each crocetin derivative as the results of formulae (1) and (2), respectively, according to formula (3).

$$\frac{A_{1cm_{Total\ crocetin\ derivative}}^{1\%}}{A_{1cm_i}^{1\%}} = \Sigma_{i=1}^n \text{Relative peak area}_i \times \quad (3)$$

Where
Relative peak area$_i$=Relative peak area of crocetin derivative i
$A_{1cm_{Total\ crocetin\ derivative}}^{1\%}$=Absorption coefficient of total crocetin derivative, defined as the theoretical absorbance of a 1% (W/V) total crocetin derivative solution in a cell of 1 cm path-length monitored at 440 nm.
$A_{1cm_i}^{1\%}$=Absorbance coefficient of crocetin derivative i, defined as the theoretical absorbance of a 1% (W/V) crocetin derivative i solution in a cell of 1 cm path-length monitored at 440 nm.
i=Fraction number of crocetin derivative
n=Total number of crocetin derivative 8. The relative content of total crocetin derivative in total pigment is calculated from the peak area of each fraction monitored at 440 nm according to formula (4).

$$C_{Total\ ester}[\%] = \frac{\Sigma_{i=1}^m Fi}{\Sigma_{j=1}^n Fj} \quad (4)$$

$$\text{Relative content}_{Total\ crocetin\ derivative} = \frac{\Sigma_{i=1}^n \text{Peak area}_i}{\Sigma_{j=1}^m \text{Peak area}_j}$$

Where
Relative content$_{Total\ crocetin\ derivative}$=Relative content of total crocetin derivative in total pigment
Peak area$_i$=Peak area of crocetin derivative i
Peak area$_j$=Peak area of fraction j
i=Fraction number of crocetin derivative
n=Total number of crocetin derivative
j=Fraction number
m=Total fraction number According to Lambert-Beer law, the amount of total crocetin derivative in *gardenia* yellow sample is calculated from the absorbance of *gardenia* yellow aqueous solution (Section A.1), the relative content of total crocetin derivative in total pigment (Section A.8) and the absorption coefficient of total crocetin derivative (Section A.7), as shown by formula (5).

$$\text{Amount}_{Total\ crocetin\ derivative}[g] = \frac{A \times \text{Relative content}_{Total\ crocetin\ derivative} \times V \times N}{A^{1\%}_{1cm\ Total\ crocetin\ derivative} \times 100} \quad (5)$$

Where
$\text{Amount}_{Total\ crocetin\ derivative}[g]$=Amount of total crocetin derivative in *gardenia* yellow sample
A=Absorbance of sample solution
V=Solvent volume for sample originally dissolving
N=Dilution fold of sample solution
Relative content$_{Total\ crocetin\ derivative}$=Relative content of total crocetin derivative in total pigment
$A^{1\%}_{1cm\ Total\ crocetin\ derivative}$=Absorption coefficient of total crocetin derivative, defined as the theoretical absorbance of a 1% (W/V) total crocetin derivative solution in a cell of 1 cm path-length monitored at 440 nm.

10. The content of total crocetin derivative in *gardenia* yellow sample is calculated from the amount of total crocetin derivative (Section A.9) and sample weight (M) (Section A.1) according to formula (6).

$$\text{Content}_{Total\ crocetin\ derivative}[\%] = \frac{\text{Amount}_{Total\ crocetin\ derivative}}{M} \times 100\% \quad (6)$$

Where
Content$_{Total\ crocetin\ derivative}$[%]=Content of total crocetin derivative in *gardenia* yellow sample
Amount$_{Total\ crocetin\ derivative}$[g]=Amount of total crocetin derivative in *gardenia* yellow sample
M=Mass of *gardenia* yellow sample B. Determination of Crocetin Derivative Composition 1. According to Lambert-Beer law, the relative content of each crocetin derivative in total crocetin derivative is calculated from the peak area (Section A.2) and absorption coefficients of each crocetin derivative (Section A.6), as shown by formula (7).

$$\text{Relative content}_i[\%] = \frac{\frac{\text{Peak area}_i}{A^{1\%}_{1cm_i}}}{\sum_{i=1}^{n} \frac{\text{Peak area}_i}{A^{1\%}_{1cm_i}}} \times 100\% \quad (7)$$

Where
Relative content$_i$=Relative content of each crocetin derivative in total crocetin derivative
Peak area$_i$=Peak area of crocetin derivative i
i=Fraction number of crocetin derivative
n=Total number of crocetin derivative 2. The amount of each crocetin derivative from *gardenia* yellow sample is calculated from the relative content of each crocetin derivative (Section B.1) and the amount of total crocetin derivative (Section A.9) according to formula (8).

$$\text{Amount}_i[g] = \text{Relative content}_i \times \text{Amount}_{Total\ crocetin\ derivative} \quad (8)$$

Where
Amount$_i$=Amount of each crocetin derivative from *gardenia* yellow sample
Relative content$_i$=Relative content of each crocetin derivative in total crocetin derivative
Amount$_{Total\ crocetin\ derivative}$=Amount of total crocetin derivative in *gardenia* yellow sample
i=Fraction number of crocetin derivative C. Determination of Crocetin Amount 1. According to formula (9), the relative crocetin content of each crocetin derivative is calculated from the molecular masses of crocetin and its derivative, 328 Da and the parent ion mass of the derivative, respectively.

$$\text{Relative crocetin content}_i = \frac{\text{Crocetin molecular mass}}{\text{Crocetin derivative molecular mass}_i} \quad (9)$$

Where
Relative crocetin content$_i$=Relative crocetin content of each crocetin derivative
Crocetin molecular mass=328 Da (Published value)
Crocetin derivative molecular mass$_i$: The molecular mass of crocetin derivative I is hereon substituted by its parent ion [M−1]⁻ mass value [m/z] from MS (Section A.4).
i=Fraction number of crocetin derivative 2. The relative crocetin content of total crocetin derivative is calculated from the relative crocetin content of each crocetin derivative (Section C.1) and its relative peak area (Section A.2) by weighted sum.

$$\text{Relative crocetin content}_{Total\ crocetin\ derivative} = \sum_{i=1}^{n} \text{Relative crocetin content}_i \times \text{Relative peak area}_i \quad (10)$$

Where
Relative crocetin content$_{Total\ crocetin\ derivative}$=Relative crocetin content of total crocetin derivative
Relative crocetin content$_i$=Relative crocetin content of each crocetin derivative
Peak area$_i$=Peak area of crocetin derivative i
i=Fraction number of crocetin derivative 3. The crocetin amount of *gardenia* yellow sample is calculated from the relative crocetin content of total crocetin derivative (Section C.2) and the amount of total crocetin derivative (Section A.9).

$$\text{Crocetin amount}[g] = \text{Relative crocetin content}_{Total\ crocetin\ derivative} \times \text{Amount}_{Total\ crocetin\ derivative} \quad (11)$$

Relative crocetin content$_{Total\ crocetin\ derivative}$=Relative crocetin content of total crocetin derivative
Amount$_{Total\ crocetin\ derivative}$=Amount of total crocetin derivative in *gardenia* yellow sample D. Recovery, Reproducibility and Minimum Detection Limit To facilitate the evaluation and acceptance of the method described in the present invention, certain amount (usually equal to the amount of crocin in sample) of external reference, crocin (Sigma, C/N:17304), is added to sample before the analysis for the recovery, reproducibility and RSD assessment of the method. Additionally, minimum detection limit is also detected with added crocin.

Data from those assessments suggested: (1) The recovery of added reference sample, crocin, was more than 97±1.61%. (2) The RSD of repeated (more than six times) experiments is less than 3.17%. This observation indicates that the method described in the invention exhibits a good reproducibility. (3) The minimum detection limit is more than 40 ng/mL on UV-VIS.

E. Advantages, Importance and Significance of the Invention

1. The invention provides a method to quantify the total amount and composition of crocetin derivative and crocetin amount from *gardenia* yellow. This effort results in the quantitative color ability and dose-effect safety evaluations of *gardenia* yellow.

2. The invention provides a method to quantify the total amount and composition of crocetin derivative and crocetin amount from *gardenia* yellow while the molecular structure of certain derivatives have not yet been elucidated and clarified.

3. The results from those three assays are fundamentally from the absorbance of the sample solution on UV-VIS. It is therefore for most individuals who work in this filed to be easy to perform while the recovery and reproducibility are also good.

The above description is intended to enable the person skilled in the science to practice the invention. It is not intended to detail all of the possible modifications and variations which will become apparent to the skilled worker upon reading the description. It is intended, however, that all such modifications and variations are included within the scope of the invention which is seen in the above description.

EXAMPLES

Following examples are presented to further explain of the analytical method described in the invention and are not to be taken as limiting in any regard.

Example 1

This example provides a preferred, but not limited, method to determine the crocetin and its derivative amounts and the derivative composition from one of commercialized *gardenia* yellow products most commonly encountered in current food additive market with relative higher absorption coefficient than others.

A. Determination of Total Crocetin Derivative Amount

In practice, *gardenia* yellow product with the label of E500 is selected as tested sample. According to procedure described as above, following steps are undertaken:

1  0.0502 g sample powder is accurately (0.0001 g) weighed. The weighed sample is then completely dissolved and makes volume to 50 mL in water. After the solution was diluted 100 times, the absorbance (A) of the solution is measured on UV-VIS spectrophotometer at 440 nm. A=0.5064 is recorded.

2. To acquire the HPLC profile of sample aqueous solution, an aliquot of *gardenia* yellow aqueous solution before dilution is filtered by 0.45□ filter and immediately for HPLC injection. With C18-HPLC, the fractions of crocetin, its derivatives and other pigments are readily separated under following conditions: Stationary phase: reversed phase C18 column (250×4.6 mm, 5 μm); Mobile phase A: Water-acetonitrile-acetic acid at 74.95:25:0.05 (V/V/V), mobile phase B: Acetonitrile; Linear gradient elution: Mobile phase B from 0 to 13.1% (V/V) in 20 minutes consequently followed by an isocratic elution from 20 to 35 minutes; Flow rate: 0.8 mL/min; Injection volume: 20 □L; Column temperature: At room temperature; Monitoring wavelength: 440 nm. The electronic absorption spectrum of each fraction is acquired from 250 to 700 nm for fraction identification if a PDA equipped. The chromatographic profile of *gardenia* yellow aqueous solution is acquired on HPLC. It is observed that each fraction is readily separated under HPLC conditions as mentioned above. The peak are of each fraction is then integrated on the chromatogram and shown in Table 1.

3. With HPLC-ACPI-MS-MS, each fraction containing crocetin structure is identified as crocetin derivative, usually as crocetin ester, on the HPLC-MS under the chromatographic conditions as outlined above and MS conditions as follow: Spray voltage: −4 Kv; Sheath gas: 30 arb; Auxiliary gas: 10 arb; Purge gas: 0 arb; Capillary temperature: 350° C.; Negative ion detection mode: Data dependency scan; CID collision energy: 35%; Fragment mass scanning range: 150-2000 (m/z). The fractions containing crocetin structure are given in Table 1.

4. The parent ion is identified of each crocetin derivative on MS. The m/z value of each parent ion is recorded in Table 1.

5. According to formula (1), the relative peak area (%) of each crocetin derivative is calculated and illustrated in Table 1.

6. The absorption coefficient ($A_{1cm_i}^{1\%}$) of each crocetin derivative is calculated from published absorption coefficient, $A_{1cm}^{1\%}=3820$ (in EtOH), of crocetin as root structure, in accordance with the negative dependence of crocetin derivative UV-VIS absorbance on its side-chain quantity and mass indicated by molecular mass, as shown in formula (2). The molecular mass of each crocetin derivative is hereon substituted by its measured parent ion [M−1]⁻ mass reading [m/z] from MS. The absorption coefficient of each crocetin derivative is given in Table 1.

7. According to formula (3), the absorption coefficient ($A_{1cm_{Total\ crocetin\ derivative}}^{1\%}$) of total crocetin derivative is calculated by weighted sum from the relative peak area and absorption coefficients of each crocetin derivative as the results of formulae (1) and (2), respectively. $A_{1cm_{Total\ crocetin\ derivative}}^{1\%}=1125$ is recorded.

8. According to formula (4), the relative content of total crocetin derivative in total pigment is calculated from the peak area of each fraction monitored at 440 nm. Relative content$_{Total\ crocetin\ derivative}=97.20\%$ is recorded.

9. According to Lambert-Beer law, the amount of total crocetin derivative in *gardenia* yellow sample is calculated from the absorbance of *gardenia* yellow aqueous solution (Section A.1), the relative content of total crocetin derivative in total pigment (Section A.8) and the absorption coefficient of total crocetin derivative (Section A.7), as shown by formula (5). Amount$_{Total\ crocetin\ derivative}=0.0225$ g is recorded.

10. According to formula (6), the content of total crocetin derivative in *gardenia* yellow sample is calculated from the amount of total crocetin derivative and sample weight. Content$_{Total\ crocetin\ derivative}=44.82\%$ is recorded.

B. Determination of Crocetin Derivative Composition

1. According to Lambert-Beer law, the relative content of each crocetin derivative in total crocetin derivative is calculated from the peak area and absorption coefficients of each crocetin derivative, as shown by formula (7). Relative content of each crocetin derivative in total crocetin derivative is shown in Table 1.

2. According to formula (8), the amount of each crocetin derivative from *gardenia* yellow sample is calculated from the relative content of each crocetin derivative and the amount of total crocetin derivative. Amount of each crocetin derivative from *gardenia* yellow sample is illustrated in Table 1.

TABLE 1

The chromatographic behaviors, MS characteristics and amounts of each fraction from *gardenia* yellow with marked absorption coefficient of 500 (E500)

| Fraction No. | Retention time [min] | Peak area [mAU * min] | Relative peak area [%] | Parent ion[m/z] | Crocetin piece[m/z] | $A_{1cm}^{1\%}$ | Relative content$_i$ [%] | Amount$_i$ [g] |
|---|---|---|---|---|---|---|---|---|
| 1 | 3.260 | 0.464 | 0.88 | | | | | |
| 2 | 4.343 | 0.201 | 0.38 | | | | | |
| 3 | 4.650 | 0.202 | 0.38 | | | | | |
| 4 | 7.093 | 26.386 | 49.92 | 1089 | 327 | 1151 | 51.19 | 0.0115 |
| 5 | 8.037 | 1.617 | 3.06 | 1089 | 327 | 1151 | 3.14 | 0.0007 |
| 6 | 9.190 | 0.507 | 0.96 | 1089 | 327 | 1151 | 0.98 | 0.0002 |
| 7 | 11.203 | 4.000 | 7.57 | 1137 | 327, 651, 813 | 1102 | 8.10 | 0.0018 |
| 8 | 14.083 | 0.075 | 0.14 | 1241 | 327 | 1010 | 0.17 | 0.0000 |
| 9 | 14.807 | 0.568 | 1.07 | 1241 | 327 | 1010 | 1.26 | 0.0003 |
| 10 | 16.073 | 1.415 | 2.68 | 1241 | 327 | 1010 | 3.13 | 0.0007 |
| 11 | 16.593 | 0.449 | 0.85 | | | | | |
| 12 | 18.150 | 0.165 | 0.31 | | | | | |
| 13 | 21.517 | 0.638 | 1.21 | 819 | 327 | 1530 | 0.93 | 0.0002 |
| 14 | 22.350 | 7.005 | 13.25 | 1241 | 327 | 1010 | 15.49 | 0.0035 |
| 15 | 23.793 | 0.527 | 1.00 | 963 | 327 | 1301 | 0.90 | 0.0002 |
| 16 | 24.597 | 0.721 | 1.36 | 1241 | 327 | 1010 | 1.59 | 0.0004 |
| 17 | 25.883 | 6.743 | 12.76 | 951 | 327 | 1318 | 11.42 | 0.0026 |
| 18 | 28.273 | 0.477 | 0.90 | 813 | 327, 651 | 1541 | 0.69 | 0.0002 |
| 19 | 28.783 | 0.694 | 1.31 | 813 | 327, 651 | 1541 | 1.01 | 0.0002 |
| Sum | | 52.854 | 100.0 | | | | 100.0 | 0.0225 |

C. Determination of Crocetin Amount

1. According to formula (9), the relative crocetin content of each crocetin derivative is calculated from the molecular masses of crocetin and its derivative, 328 Da and the parent ion mass of the derivative, respectively. Relative crocetin content of each crocetin derivative is given in Table 2.

2. The relative crocetin content of total crocetin derivative is calculated from the relative crocetin content of each crocetin derivative and its relative peak area by weighted sum. The relative crocetin content of total crocetin derivative is 29.35%.

3. The crocetin amount of *gardenia* yellow is calculated from the relative crocetin content of total crocetin derivative and the amount of total crocetin derivative. The crocetin amount of total crocetin derivative in the *gardenia* yellow sample (0.0502 g) is 0.0066 g. The crocetin amount of *gardenia* yellow is 13.15%.

TABLE 2

The chromatographic behaviors, MS characteristics and crocetin content of each fraction from *gardenia* yellow with marked absorption coefficient of 500 (E500)

| Fraction No. | Retention time [min] | Peak area [mAU * min] | Relative peak area [%] | Parent ion [m/z] | Crocetin piece [m/z] | Relative crocetin centent i | Relative content$_i$ [%] |
|---|---|---|---|---|---|---|---|
| 1 | 3.26 | 0.464 | 0.88 | | | | |
| 2 | 4.343 | 0.201 | 0.38 | | | | |
| 3 | 4.65 | 0.202 | 0.38 | | | | |
| 4 | 7.093 | 26.386 | 49.92 | 1089 | 327 | 0.3002 | 14.99 |
| 5 | 8.037 | 1.617 | 3.06 | 1089 | 327 | 0.3002 | 0.92 |
| 6 | 9.19 | 0.507 | 0.96 | 1089 | 327 | 0.3002 | 0.29 |
| 7 | 11.203 | 4 | 7.57 | 1137 | 327 | 0.2875 | 2.18 |
| 8 | 14.083 | 0.075 | 0.14 | 1241 | 327 | 0.2634 | 0.04 |
| 9 | 14.807 | 0.568 | 1.07 | 1241 | 327 | 0.2634 | 0.28 |
| 10 | 16.073 | 1.415 | 2.68 | 1241 | 327 | 0.2634 | 0.71 |
| 11 | 16.593 | 0.449 | 0.85 | | | | |
| 12 | 18.15 | 0.165 | 0.31 | | | | |
| 13 | 21.517 | 0.638 | 1.21 | 819 | 327 | 0.3992 | 0.48 |
| 14 | 22.35 | 7.005 | 13.25 | 1241 | 327 | 0.2634 | 3.49 |
| 15 | 23.793 | 0.527 | 1 | 963 | 327 | 0.3395 | 0.34 |
| 16 | 24.597 | 0.721 | 1.36 | 1241 | 327 | 0.2634 | 0.36 |
| 17 | 25.883 | 6.743 | 12.76 | 951 | 327 | 0.3438 | 4.39 |
| 18 | 28.273 | 0.477 | 0.9 | 813 | 327 | 0.4022 | 0.36 |
| 19 | 28.783 | 0.694 | 1.31 | 813 | 327 | 0.4022 | 0.53 |
| Sum | | | | | | | 29.35 |

D. Recovery and Reproducibility

To facilitate the evaluation and acceptance of the method described in the present invention, certain amount (usually equal to the amount of crocin in sample) of external reference, crocin (Sigma, C/N:17304), is added to sample before the analysis for the recovery, reproducibility and RSD assessment of the method. Additionally, minimum detection limit is also detected with added crocin.

Data from those assessments suggested: (1) The recovery of added reference sample, crocin, was more than 97±1.61%. (2) The RSD of repeated (more than six times) experiments is less than 3.17%. This observation indicates that the method described in the invention exhibits a good reproducibility.

This method is preferably employed to perform the determination of total amount and composition of crocin derivative and crocin amount of product with relative higher pigment concentration for its safety evaluation and quality control schemes.

Example 2

This example provides a preferred, but not limited, method to determine the crocin and its derivative amounts and the derivative composition from one of commercialized gardenia yellow products most commonly encountered in current food additive market with relative lower absorption coefficient than others.

A. Determination of Total Crocetin Derivative Amount

In practice, gardenia yellow product with the label of E450 is selected as tested sample. According to procedure described as above, following steps are undertaken:

1 0.0531 g sample powder is accurately (0.0001 g) weighed. The weighed sample is then completely dissolved and makes volume to 50 mL in water. After the solution was diluted 100 times, the absorbance (A) of the solution is measured on UV-VIS spectrophotometer at 440 nm. A=0.4971 is recorded.

2. To acquire the HPLC profile of sample aqueous solution, an aliquot of gardenia yellow aqueous solution before dilution is filtered by 0.45□ filter and immediately for HPLC injection. With C18-HPLC, the fractions of crocin, its derivatives and other pigments are readily separated under following conditions: Stationary phase: reversed phase C18 column (250×4.6 mm, 5 μm); Mobile phase A: Water-acetonitrile-acetic acid at 74.95:25:0.05 (V/V/V), mobile phase B: Acetonitrile; Linear gradient elution: Mobile phase B from 0 to 13.1% (V/V) in 20 minutes consequently followed by an isocratic elution from 20 to 35 minutes; Flow rate: 0.8 mL/min; Injection volume: 20 □L; Column temperature: At room temperature; Monitoring wavelength: 440 nm. The electronic absorption spectrum of each fraction is acquired from 250 to 700 nm for fraction identification if a PDA equipped. The chromatographic profile of gardenia yellow aqueous solution is acquired on HPLC. It is observed that each fraction is readily separated under HPLC conditions as mentioned above. The peak are of each fraction is then integrated on the chromatogram and shown in Table 3.

3. With HPLC-ACPI-MS-MS, each fraction containing crocetin structure is identified as crocetin derivative, usually as crocetin ester, on the HPLC-MS under the chromatographic conditions as outlined above and MS conditions as follow: Spray voltage: −4 Kv; Sheath gas: 30 arb; Auxiliary gas: 10 arb; Purge gas: 0 arb; Capillary temperature: 350° C.; Negative ion detection mode: Data dependency scan; CID collision energy: 35%; Fragment mass scanning range: 150-2000 (m/z). The fractions containing crocetin structure are given in Table 3.

4. The parent ion is identified of each crocetin derivative on MS. The m/z value of each parent ion is recorded in Table 3.

5. According to formula (1), the relative peak area (%) of each crocetin derivative is calculated and illustrated in Table 3.

6. The absorption coefficient ($A_{1cm_i}^{1\%}$) of each crocetin derivative is calculated from published absorption coefficient, $A_{1cm}^{1\%}=3820$ (in EtOH), of crocetin as root structure, in accordance with the negative dependence of crocetin derivative UV-VIS absorbance on its side-chain quantity and mass indicated by molecular mass, as shown in formula (2). The molecular mass of each crocetin derivative is hereon substituted by its measured parent ion [M−1]⁻ mass reading [m/z] from MS. The absorption coefficient of each crocetin derivative is given in Table 3.

7. According to formula (3), the absorption coefficient ($A_{1cm_{Total\ crocetin\ derivative}}^{1\%}$) of total crocetin derivative is calculated by weighted sum from the relative peak area and absorption coefficients of each crocetin derivative as the results of formulae (1) and (2), respectively. $A_{1cm_{Total\ crocetin\ derivative}}^{1\%}=1127$ is recorded.

8. According to formula (4), the relative content of total crocetin derivative in total pigment is calculated from the peak area of each fraction monitored at 440 nm. Relative content$_{Total\ crocetin\ derivative}=99.09\%$ is recorded.

9. According to Lambert-Beer law, the amount of total crocetin derivative in gardenia yellow sample is calculated from the absorbance of gardenia yellow aqueous solution (Section A.1), the relative content of total crocetin derivative in total pigment (Section A.8) and the absorption coefficient of total crocetin derivative (Section A.7), as shown by formula (5). Amount$_{Total\ crocetin\ derivative}=0.0221$ g is recorded.

10. According to formula (6), the content of total crocetin derivative in gardenia yellow sample is calculated from the amount of total crocetin derivative and sample weight. Content$_{Total\ crocetin\ derivative}=41.62\%$ is recorded.

B. Determination of Crocetin Derivative Composition

1. According to Lambert-Beer law, the relative content of each crocetin derivative in total crocetin derivative is calculated from the peak area and absorption coefficients of each crocetin derivative, as shown by formula (7). Relative content of each crocetin derivative in total crocetin derivative is shown in Table 3.

2. According to formula (8), the amount of each crocetin derivative from gardenia yellow sample is calculated from the relative content of each crocetin derivative and the amount of total crocetin derivative. Amount of each crocetin derivative from gardenia yellow sample is illustrated in Table 3.

TABLE 3

The chromatographic behaviors, MS characteristics and amounts of each fraction from *gardenia* yellow with marked absorption coefficient of 450 (E450)

| Fraction No. | Retention time[min] | Peak area [mAU * min] | Relative peak area[%] | Parent ion[m/z] | Crocetin piece[m/z] | $A_{1cmi}^{1\%}$ | Relative amount$_i$ [%] | Amount$_i$ [g] |
|---|---|---|---|---|---|---|---|---|
| 1 | 4.343 | 0.269 | 0.40 | | | | | |
| 2 | 4.607 | 0.265 | 0.40 | | | | | |
| 3 | 4.743 | 0.018 | 0.03 | | | | | |
| 4 | 5.107 | 0.395 | 0.59 | 1173 | 327, 651, 813, | 1068 | 0.63 | 0.0001 |
| 5 | 5.773 | 0.055 | 0.08 | | | | | |
| 6 | 7.083 | 49.324 | 73.85 | 1089 | 327 | 1151 | 73.43 | 0.0162 |
| 7 | 8.010 | 1.943 | 2.91 | 1089 | 327 | 1151 | 2.89 | 0.0006 |
| 8 | 9.173 | 0.889 | 1.33 | 1089 | 327 | 1151 | 1.32 | 0.0003 |
| 9 | 11.227 | 4.274 | 6.40 | 1137 | 327, 651, 813 | 1102 | 6.64 | 0.0015 |
| 10 | 14.873 | 0.785 | 1.18 | 1241 | 327 | 1010 | 1.33 | 0.0003 |
| 11 | 16.143 | 2.029 | 3.04 | 1241 | 327 | 1010 | 3.44 | 0.0008 |
| 12 | 21.587 | 0.263 | 0.39 | 819 | 327 | 1530 | 0.29 | 0.0001 |
| 13 | 22.407 | 4.765 | 7.13 | 1241 | 327 | 1010 | 8.08 | 0.0018 |
| 14 | 24.703 | 0.158 | 0.24 | 1241 | 327 | 1010 | 0.27 | 0.0001 |
| 15 | 25.975 | 0.754 | 1.13 | 951 | 327 | 1318 | 0.98 | 0.0002 |
| 16 | 28.890 | 0.604 | 0.90 | 813 | 327, 651 | 1541 | 0.67 | 0.0001 |
| Sum | | 66.790 | 100.0 | | | | 100.0 | 0.0221 |

C. Determination of Crocetin Amount

1. According to formula (9), the relative crocetin content of each crocetin derivative is calculated from the molecular masses of crocetin and its derivative, 328 Da and the parent ion mass of the derivative, respectively. Relative crocetin content of each crocetin derivative is given in Table 4.

2. The relative crocetin content of total crocetin derivative is calculated from the relative crocetin content of each crocetin derivative and its relative peak area by weighted sum. The relative crocetin content of total crocetin derivative is 29.41%.

3. The crocetin amount of *gardenia* yellow is calculated from the relative crocetin content of total crocetin derivative and the amount of total crocetin derivative. The crocetin amount of total crocetin derivative in the *gardenia* yellow sample (0.0502 g) is 0.0065 g. The crocetin amount of *gardenia* yellow is 12.24%.

D. Recovery and Reproducibility

To facilitate the evaluation and acceptance of the method described in the present invention, certain amount (usually equal to the amount of crocin in sample) of external reference, crocin (Sigma, C/N:17304), is added to sample before the analysis for the recovery, reproducibility and RSD assessment of the method. Additionally, minimum detection limit is also detected with added crocin.

Data from those assessments suggested: (1) The recovery of added reference sample, crocin, was more than 96±2.12%. (2) The RSD of repeated (more than six times) experiments is less than 4.03%. This observation indicates that the method described in the invention exhibits a good reproducibility.

This method is preferably employed to perform the determination of total amount and composition of crocetin

TABLE 4

The chromatographic behaviors, MS characteristics and crocetin content of each fraction from *gardenia* yellow with marked absorption coefficient of 450 (E450)

| Fraction No. | Retention time [min] | Peak area [mAU * min] | Relative peak area [%] | Parent ion [m/z] | Crocetin piece [m/z] | Relative crocetin centent i | Relative content$_i$ [%] |
|---|---|---|---|---|---|---|---|
| 1 | 4.343 | 0.269 | 0.4 | | | | |
| 2 | 4.607 | 0.265 | 0.4 | | | | |
| 3 | 4.743 | 0.018 | 0.03 | | | | |
| 4 | 5.107 | 0.395 | 0.59 | 1173 | 327 | 0.2788 | 0.16 |
| 5 | 5.773 | 0.055 | 0.08 | | | | |
| 6 | 7.083 | 49.324 | 73.85 | 1089 | 327 | 0.3003 | 22.18 |
| 7 | 8.01 | 1.943 | 2.91 | 1089 | 327 | 0.3003 | 0.87 |
| 8 | 9.173 | 0.889 | 1.33 | 1089 | 327 | 0.3003 | 0.40 |
| 9 | 11.227 | 4.274 | 6.4 | 1137 | 327 | 0.2876 | 1.84 |
| 10 | 14.873 | 0.785 | 1.18 | 1241 | 327 | 0.2635 | 0.31 |
| 11 | 16.143 | 2.029 | 3.04 | 1241 | 327 | 0.2635 | 0.80 |
| 12 | 21.587 | 0.263 | 0.39 | 819 | 327 | 0.3993 | 0.16 |
| 13 | 22.407 | 4.765 | 7.13 | 1241 | 327 | 0.2635 | 1.88 |
| 14 | 24.703 | 0.158 | 0.24 | 1241 | 327 | 0.2635 | 0.06 |
| 15 | 25.975 | 0.754 | 1.13 | 951 | 327 | 0.3438 | 0.39 |
| 16 | 28.89 | 0.604 | 0.9 | 813 | 327 | 0.4022 | 0.36 |
| Sum | | | | | | | 29.41 | derivative and crocetin amount of product with relative lower pigment concentration for its safety evaluation and quality control schemes.

Finally, it should be noted that: Obviously, the examples described above intend only to illustrate the invention clearly and not limitations to provide a way to implement the invention. For the individuals who are skilled in the related fields of science, various changes, modifications or variations in the invention based on description as above can also be made. There is no need to implement all the way or to be exhaustive to raise any other examples. Any change or variation in the invention is still in the protection scope of the invention.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based can be readily utilized as a basis for the design of other structures, methods, and systems for carrying out the several purposes of the embodiments and claims presented in this application. It is important, therefore, that the claims be regarded as including such equivalent constructions.

We claim:

1. A method for the determination of total amount and composition of the Crocetin derivatives in the *gardenia* yellow product, the method comprising the steps of:
   (i) determining the absorbance of the *gardenia* yellow sample comprising weighing the sample of M grams of *gardenia* yellow, dissolving at constant volume (V) ml of water, diluting the solution by N times and measuring absorbance A of dilution on a UV-VIS spectrophotometer at 440 nm wavelength;
   (ii) obtaining a chromatogram of the sample; the chromatogram of the sample being obtained by high performance liquid chromatography; chromatographic conditions comprising a stationary phase being a C18 column having dimensions of 250×4.6 mm i.d., 5 μm; a mobile phase A being water-acetonitrile-acetic acid, a volume ratio being 74.95:25:0.05; a mobile phase B being acetonitrile; performing a linear gradient elution method comprising increasing mobile phase B from 0 to 13.3% (V/V) in 20 minutes, maintaining the mobile phase B between 20-35 minutes at 13.3% (V/V), comprising a flow rate of 0.8 ml/min, an injection volume of 20 μL, the column temperature being room temperature; detection wavelength of 440 nm; for each component, performing integration to obtain peak area;
   (iii) identifying the components containing the Crocetin structure comprising performing HPLC-MS-MS, identifying in the components containing the Crocetin structure by studying the chromatogram, chromatographic conditions same as step (ii); mass spectrometry conditions, the mass spectrometry conditions comprising a spray voltage of −4 Kv, a sheath gas of 30 arb, an Aux gas of 10 arb, a purge gas of 0 arb, a capillary temperature of 350° C.; a negative ion detection mode; a data dependency scanning; a CID collision energy of 35%, the detection range of the debris mass m/z being from 150 to 2000;
   (iv) recording the m/z values of molecular ion peaks of the structural components containing: identifying molecular ion peaks on a first-order mass spectrum and recording molecular ion peak m/z of each component containing the Crocetin structure;
   (v) calculating the relative proportions of the peak areas of the components of each of the Crocetin derivatives comprising implementing Formula (1):

$$F'_i [\%] = \frac{F_i}{\sum_{i=1}^{n} F_i} \times 100\% \tag{1}$$

wherein $F'_i$ is a relative proportion of the peak area of component i containing the Crocetin structure, $F_i$ is a peak area of component i, and n is a number of components containing the Crocetin structure;
   (vi) calculating a concentration absorbance coefficient of each of the Crocetin derivatives wherein a published concentration absorbance coefficient of the Crocetin of $A_{1cm}^{1\%}=3820$ (methanol), according to formula (2), calculating a concentration absorbance coefficient of each component containing the Crocetin structure:

$$A_{1cm_i}^{1\%} = A_{1cm_c}^{1\%} \times \frac{MW_C}{MW_i} \tag{2}$$

wherein $A_{1cm_i}^{1\%}$ is concentration absorbance coefficient of the component i containing the Crocetin structure, defined as absorbance of the 1% (w/w) sample solution at a wavelength of 440 nm in a 1 cm colorimetric cup, and $A_{1cm_c}^{1\%}$ is the concentration absorbance coefficient of the Crocetin at 440 nm, $A_{1cm_c}^{1\%}=3820$ (methanol); i is the index of the composition containing the Crocetin structure; $MW_c$ is the molecular weight of the Crocetin [Da]; $MW_i$ is the molecular weight [Da] of the component i containing the Crocetin structure, using the m/z value of the molecular ion peak of the component;
   (vii) calculating a concentration absorbance coefficient of total content of the Crocetin derivative in the *gardenia* yellow product comprising obtaining results of the calculation of the formulas (1) and (2), implementing formula (3), comprising using the Weighted Sum Method to calculate a concentration absorbance coefficient of a total number of the Crocetin derivatives in the weight of the *gardenia* yellow:

$$A_{1cm_{Total}}^{1\%} = \sum_{i=1}^{n} F'_i A_{1cm_i}^{1\%} \tag{3}$$

wherein, $A_{1cm_{Total}}^{1\%}$ is a concentration absorbance coefficient of total number of the Crocetin derivative, and $F'_i$ is a relative ratio of the peak area of component i containing the Crocetin structure; $A_{1cm_i}^{1\%}$ is a concentration absorbance coefficient of the component i containing the Crocetin structure, defined as absorbance value of the 1% (w/w) sample solution in 1 cm optical path of a colorimetric tank at 440 nm, i is an index of the composition containing the Crocetin structure, n is a number of components containing the Crocetin structure;

(viii) calculating a relative content of total Crocetin derivatives in a total pigment comprising implementing to formula (4)

$$M'_{Total} = \frac{\sum_{i=1}^{n} F_i}{\sum_{j=1}^{m} F_j} \quad (4)$$

wherein $M'_{Total}$ is the relative content of total Crocetin derivative in the total pigment, $F_i$ is a peak area of component i containing the Crocetin structure, n is a number of peaks of components containing the Crocetin structure, $F_j$ is a peak area of the absorbed component j at 440 nm, and m is a number of the absorbing component at 440 nm;

(ix) calculating a total Crocetin derivative in the *gardenia* yellow sample; according to the formula (1), the formula (3) and the formula (4), and further calculating a total of the Crocetin's derivative in the *gardenia* yellow by implementing formula (5):

$$M_{Total}[g] = \frac{A M'_{Total} V[mL] N}{A^{1\%}_{1cm_{Total}} \times 100} \quad (5)$$

wherein $M_{Total}$ is a total content of the Crocetin derivative in the *gardenia* yellow sample; A is a absorbance value of the sample solution; $A^{1\%}_{1cm_{Total}}$ is a concentration absorbance coefficient of the total Crocetin derivative; V is a volume of the sample; N is a dilution multiple of the solution;

(x) calculating a relative content of total Crocetin derivatives in *gardenia* yellow samples comprising implementing formula (6)

$$M''_{Total}[\%] = \frac{M_{Total}}{M} \times 100\% \quad (6)$$

wherein $M''_{Total}$ is a relative content of total Crocetin derivative in the *gardenia* yellow sample, $M_{Total}$ is a total content of the Crocetin derivative in the *gardenia* yellow sample, and M is a mass of the *gardenia* yellow sample;

(xi) calculating a relative mass of each of the Crocetin derivatives in the gardenia yellow sample comprising implementing formula (7), according to the peak area of each component on the HPLC chromatogram, $$M'_i[\%] = \frac{\frac{F_i}{A^{1\%}_{1cm_i}}}{\sum_{i=1}^{n} \frac{F_i}{A^{1\%}_{1cm_i}}} \times 100\% \quad (7)$$

wherein $M'_i[\%]$ is a relative mass of the component i containing the Crocetin structure, $A_{1cm_j}^{1\%}$ is a concentration of the absorbance coefficient of the component i containing the Crocetin structure, $F_i$ is a peak area of the component i containing the Crocetin structure, and n is a number of components containing the Crocetin structure;

(xii) calculating a mass of each of the Crocetin derivatives in the *gardenia* yellow sample; comprising implementing formula (8)

$$M_i[g] = M'_i M_{Total} \quad (8)$$

wherein $M_i$ is a mass of the component i containing the Crocetin structure, $M'_i$ is a relative mass of the component i containing the Crocetin structure, i is a number of the of the Crocetin component, $M_{Total}$ is a total content of the Crocetin derivative in the *gardenia* yellow sample.

* * * * *